United States Patent [19]
Yagi et al.

[11] 4,182,765
[45] Jan. 8, 1980

[54] OIL SOLUBLE FUNGICIDE OBTAINED FROM THE REACTION OF A QUATERNARY AMMONIUM SALT AND AN ALKYL BENZENE SULFONIC ACID

[75] Inventors: Osami Yagi, Tokyo; Yasuo Fujiwara, Yokohama, both of Japan

[73] Assignee: Nippon Oil Company Limited, Tokyo, Japan

[21] Appl. No.: 683,932

[22] Filed: May 6, 1976

Related U.S. Application Data

[63] Continuation-in-part of Ser. No. 375,025, Jun. 29, 1973, abandoned.

[51] Int. Cl.$^2$ ............ A01N 9/22; C07D 213/04
[52] U.S. Cl. ............ 424/263; 260/567.6 M; 424/329; 546/347
[58] Field of Search ............ 260/294.8 R, 457, 567.6, 260/567.6 M; 424/329, 263; 546/347

[56] References Cited
U.S. PATENT DOCUMENTS 2,519,924  8/1950  Newak ............ 260/567.6 M

OTHER PUBLICATIONS

Schwartz et al., Surface Active Agents and Detergents, vol. II, Interscience Pub., pp. 78–81 & 84–87, (1958).
Karrer, Organic Chemistry, 4th English Edition, Elsevier Pub., p. 928.

Primary Examiner—Alan L. Rotman
Assistant Examiner—Richard A. Schwartz
Attorney, Agent, or Firm—Scully, Scott, Murphy & Presser

[57] ABSTRACT

This invention provides an oil soluble fungicide comprising a compound having the general formula

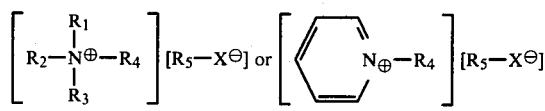

wherein $R_1$ is a mononuclear aromatic hydrocarbon radical comprising up to 22 carbon atoms, $R_2$ and $R_3$, which may be the same or different, each represents an aliphatic hydrocarbon radicals comprising up to 8 carbon atoms, $R_4$ is an aliphatic hydrocarbon radical comprising from 8 to 20 carbon atoms; $R_5$ is an alkylbenzene radical in which the alkyl group contains from 10 to 14 carbon atoms; and $X^\ominus$ is a sulfonate radical.

14 Claims, No Drawings

OIL SOLUBLE FUNGICIDE OBTAINED FROM THE REACTION OF A QUATERNARY AMMONIUM SALT AND AN ALKYL BENZENE SULFONIC ACID

CROSS REFERENNCE TO RELATED APPLICATION

This application is a continuation-in-part of our prior filed application Ser. No. 375,025 filed June 29, 1973, now abandoned.

BACKGROUND OF THE INVENTION

1. Field of the Invention

This invention relates to a novel complex compound type oil soluble fungicide comprising a complex compound of quaternary ammonium.

2. Description of the Prior Art

It is a well known fact that some quaternary ammonium salts such as alkyl-substituted quaternary ammonium chloride have a strong sterilizing power in an aqueous solution. As a result, these quaternary ammonium salts are widely used as fungicides. However, the quaternary ammonium salts, though well soluble in water, are not suitable as fungicides to be used for oleophilic materials, because they are hardly soluble in such oleophilic materials as fat, hydrocarbon oil, high molecular compounds and the like.

Heretofore, it has been said that the quaternary ammonium salt type fungicide, which is a cation surface active agent, considerably loses its sterilizing power by the presence of an anion surface active agent and that its use together with soap and the like is not desirable.

SUMMARY OF THE INVENTION

It is now found that a quaternary ammonium salt type cation fungicide can retain sterilizing power and have also oil solubility by selecting a suitable anion surface active agent and then reacting it with the quaternary ammonium salt type cation surface active agent.

In other words, this invention is based on the discovery that the above quaternary ammonium complex compound is oil soluble and highly sterilizing.

DESCRIPTION OF THE INVENTION

The complex compound type oil soluble fungicide according to this invention is a novel material with many superior properties so as to be widely used for various purposes. Because of its oil solubility, it is suitable as a fungicide for protecting oil products such as jet fuel, kerosene, gas oil, fuel oil and lubricating oil from harmful effects by fungi. It is also effectively used as a fungicide for protecting natural and synthetic high molecular compounds such as fiber, paint, plastic and rubber from harmful effects by fungi. The complex compound type oil soluble fungicide according to this invention is also characterized by its anticorrosive rather than corrosive action upon such metals as copper, steel and aluminum by the effect of the combined surface active agent.

The fungicide of this invention is used according to purposes in the concentration of 10–10,000 ppm. In general, however, its use at 50 ppm of concentration can obtain a satisfactory sterilizing effect. Therefore, properties of the object material suffer almost no change by adding this fungicide, which is also effective when used at such a low concentration as stated above.

The complex compound type oil soluble fungicide as referred to in this invention has the following structure of a complex compound:

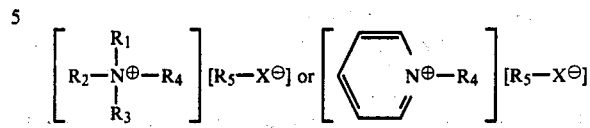

wherein

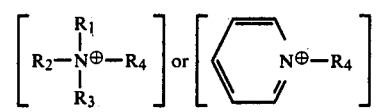

is a cation constituting portion;

is an anion constituting portion; N is nitrogen atom; $R_1$ is a mononuclear aromatic hydrocarbon radical comprising up to 22 carbon atoms, $R_2$ and $R_3$, which may be the same or different, each represents an aliphatic hydrocarbon radicals comprising up to 8 carbon atoms, $R_4$ is an aliphatic hydrocarbon radical comprising from 8 to 20 carbon atoms; $R_5$ is an alkylbenzene radical in which the alkyl group contains from 10 to 14 carbon atoms; and $X^\ominus$ is a sulfonate radical.

The complex compound type oil soluble fungicide of this invention is synthesized by mixing and reacting an aqueous solution of a quaternary ammonium salt providing the cation constituting portion with an aqueous solution of a sulfonate salt preferably at normal temperature and under normal pressure. The reaction temperature is not particularly restricted. In general, however, temperatures within the range of $-10°$ to $300°$ C. are available. The reaction rate is decreased if the temperature is lower than the above range, while the temperature exceeding this range is also undesirable because of causing side-reactions such as decomposition.

The quaternary ammonium salt referred to in this invention includes varius salts such as halide, sulfate, phosphate and nitrate of quaternary ammonium, for example, chloride, bromide, sulfate, nitrate or acetate of alkyl (mixed alkyl having 8–18 carbon atoms)—dimethylbenzylammonium, cetyl-methyl-ethylbenzylammonium, cetyl-dimethyldodecylbenzylammonium and cetyl-pyridinium.

On the other hand, the sulfonates used in this invention are, for example, various salts of straight- or branched-chain alkyl (mixed alkyl having 10–14 carbon atoms) benzenesulfonic acid, decylbenzenesulfonic acid, dodecylbenzenesulfonic acid, and tetradecylbenzenesulfonic acid, such as alkali metal salts and alkaline earth metal salts thereof.

The reason why alkylbenzenesulfonate in which the alkyl group contains from 10 to 14 carbon atoms is selected as mentioned above as the anion agent to be used in the present invention may be clearly understood from the results of Experiments shown in the following Table 1.

First, when alkylbenzenesulfonate in which the alkyl group contains not more than 8 carbon atoms is used, the reaction product is oil-insoluble. Secondly, the sterilizing effect on fungi and bacteria of a reaction product obtained by using alkylbenzesulfonate in which the alkyl group contains 16 carbon atoms is somewhat inferior to that of a reaction product obtained by using alkylbenzenesulfonate in which the alkyl group contains not more than 14 carbon atoms.

Therefore, in order to obtain an oil-soluble fungicide having a high sterilizing effect, it is necessary as mentioned above that alkylbenzenesulfonate in which the alkyl group contains from 10 to 14 carbon atoms be used as anion agent as in the present invention.

grams of 10% aqueous solution of alkyldimethylbenzylammonium chloride (the alkyl group was a mixture having 8-18 carbon atoms), followed by shaking for 1 minute at room temperature. After further adding 350 ml. of benzene, shaking for 2 minutes and leaving still, the benzene layer was separated to remove the benzene by evaporating under a reduced pressure. Thus, the white reaction product was obtained at 95% of yield on the basis of the theoretical value. The product having a melting point of 83°-84° C. was identified as dodecyl- Table 1

| Experiment No. | Cation agent used | Number of carbon atoms contained in alkyl group in alkylbenzenesulfonate used as anion agent | Kerosene-solubility of reaction product | Sterilizing effect (by cultivation at 30° C. for 90 days) | | | | | | |
|---|---|---|---|---|---|---|---|---|---|---|
| | | | | Cladosporium sp. | Penicillium sp. | Aspergillus sp. | Fusarium sp. | Paecilomyces sp. | C Candida sp. | Pseudomonas sp. |
| 1 | Alkyl($C_8$-$C_{18}$)-dimethyl-benzyl ammonium chloride | 6 | insoluble | ---------- Test was not conducted. -------------- | | | | | | |
| 2 | | 8 | insoluble | ---------------- Same as above. ------------------ | | | | | | |
| 3 | | 10 | soluble | ----- No growth of fungi and bacteria was observed. ------ | | | | | | |
| 4 | | 12 | soluble | ---------------- Same as above. ------------------ | | | | | | |
| 5 | | 14 | soluble | ---------------- Same as above. ------------------ | | | | | | |
| 6 | | 16 | soluble | No growth of f. and b. was observed | No growth of f. and b. was observed | No growth of f. and b. was observed | Small quantity of f. and b. grew. | No growth of f. and b. was observed | No growth of f. and b. was observed | Small quantity of f. and b. grew. |

The sterilizing effect on fungi and bacteria of the fungicides in the above Experiments 3-6 were tested according to the same method as in the following Examples by adding 50 ppm. of each of the products to fuel oil used as mineral oil.

The quaternary ammonium salt can react with the sulfonate salt in the concentration of 0.1-50% by weight. Generally, however, it is suitable to conduct the reaction in the concentration of about 1-10% by weight. If sufficiently soluble in water, the anionic material may not be used in the form of salt. The anionic material can be used, as occasion demands, singly or as a mixture. The reaction product is hardly soluble in water so as to be separated or dispersed as a precipitate or colloid in an aqueous solution. Therefore, the product can be separated directly after leaving still. However, it can be easily extracted by adding an organic solvent insoluble in water such as benzene or hexane to the reaction system. The extracted reaction product is isolated in the form of paste, wax, oil or solid by removing the organic solvent.

The reaction product synthesized and isolated as stated above has a strong sterilizing power, which has been proved by the following test. That is, the reaction product to be tested was dissolved in the mineral oil wherein fungi could grow. After adding an inorganic culture medium containing N, P, K, Fe, Mg and others to the resulting solution, fungi eating mineral oil were incubated in the medium for the purpose of examining the state of growth of the fungi and the sterilizing power of the fungicide.

DESCRIPTION OF PREFERRED EMBODIMENTS

The following Examples are illustrative of this invention in further detail but are not intended to limit the scope thereof;

Examples for producing the complex used in this invention (Experiment 1)

350 grams of 10% aqueous solution of straight-chain sodium dodecylbenzenesulfonate were added to 354 benzenesulfonic acid complex of alkyldimethylbenzylammonium by infrared spectroscopic and NMR analyses.

(Experiment 2)

350 grams of 10% aqueous solution of branched-chain type sodium dodecylbenzenesulfonate were added to 382 grams of 10% aqueous solution of alkyldimethylbenzylammonium chloride (the alkyl group was a mixture having 8-22 carbon atoms), followed by shaking for 1 minute at about 20° C. After further adding 350 ml. of hexane, shaking for 2 minutes and leaving still, the hexane layer was separated to remove the hexane by evaporating under a reduced pressure. The white reaction product having a melting point of 86°-87° C. was obtained at 94% of yield on the basis of the theoretical value. The product was identified as dodecylbenzenesulfonic acid complex of alkyldimethylbenzylammonium by the same analyses as those in Example 1.

(Experiment 3)

350 grams of 10% aqueous solution of straight-chain potassium dodecylbenzenesulfonate were added to 338 grams of 10% aqueous solution of cetylpyridinium chloride, followed by shaking for 1 minute at about 50° C. Then, 350 ml. of benzene were added, followed by further shaking for 2 minutes. After leaving still, the benzene layer was separated to remove the benzene by evaporating under a reduced pressure. Thus, the yellow reaction product (having a melting point of 90°-91° C.) was obtained at 95% or above of yield on the basis of the theoretical value. By the same analyses as those in Experiment 1, the product was identified as dodecylbenzene-sulfonic acid complex of cetylpyridinium.

(Experiment 4)

370 grams of 5% aqueous solution of straight-chain sodium tetradecylbenzenesulfonate were added to 350 grams of 5% aqueous solution of alkyldimethylbenzylammonium chloride (the alkyl group was a mixture having 8-18 carbon atoms), followed by shaking for 1 minute at about 30° C. After further adding 350 ml. of benzene, shaking for 2 minutes and leaving still, the benzene layer was separated to remove the benzene by evaporating under a reduced pressure. The yellow reaction product was obtained at 94% of yield on the basis of the theoretical value. The product was identified as tetradecylbenzenesulfonic acid complex of alkyl dimethylbenzylammonium by the same analyses as those in Experiment 1.

(Experiment 5)

320 grams of 10% aqueous solution of straight-chain sodium decylbenzenesulfonate were added to 354 grams of 10% aqueous solution of alkyldimethylbenzylammonium chloride (the alkyl group was a mixture having 8-18 carbon atoms), followed by shaking for 1 minute at room temperature. After further adding 300 ml. of benzene, shaking for 2 minutes and leaving still, the benzene layer was separated to remove the benzene by evaporating under a reduced pressure. The yellow reaction product was obtained at 96% of yield on the basis of the theoretical value. The product was identified as decylbenzenesulfonic acid complex of alkyldimethylbenzylammonium.

(Experiment 6)

In the same manner as Experiment 1, the reaction was conducted at room temperature by using alkyldimethylbenzylammonium chloride (the alkyl group was a mixture having 8-18 carbon atoms) and straight-chain sodium alkylbenzenesulfonate (the alkyl group was a mixture having 10-14 carbon atoms) as starting materials to obtain yellow solid of alkylbenzenesulfonic acid complex of alkyldimethylbenzylammonium at 96% of yield on the basis of the theoretical value.

(Experiment 7)

345 grams of 5% aqueous solution of straight-chain sodium alkylbenzenesulfonate (the alkyl group was a mixture having 10-14 carbon atoms) were added to 338 grams of 5% aqueous solution of cetylpyridinium chloride, followed by shaking for 1 minute at room temperature. Then, 350 ml. of hexane were added, followed by further shaking for 2 minutes. After leaving still, the hexane layer was separated to remove the hexane by evaporating under a reduced pressure. Thus, the yellow solid of alkylbenzenesulfonic acid complex of cetylpyridinium was obtained at 95% of yield on the basis of the theoretical value.

Examples 1-7 and Comparative Example 1

The test for examining sterilizing power of the complex compound type oil soluble fungicide synthesized by Experiments 1-7 was conducted according to the following process. The complex compound type oil soluble fungicide was dissolved in kerosene, jet fuel, gas oil, fuel oil and lubricating oil so that the resulting solution had the predetermined concentration. 2 ml. of this solution were added to a test tube having 18 mm. of the inside diameter. After further adding 2 ml. of inorganic culture medium containing 3 grams of $NaNO_3$, 1.0 gram of $K_2HPO_4$, 0.5 grams of KCl, 0.5 grams of $MgSO_4.7H_2O$ and 0.01 gram of $FeSO_4$ to 1 liter of distilled water, fungi belonging to Cladosporium sp., Penicillium sp., Aspergillus sp., Fusarium sp., Paecilomyces sp., Candida sp., and bacteria belonging to Pseudomonas sp. which can eat kerosene, jet fuel, gas oil, fuel oil and lubricating oil were incubated to conduct the cultivation by leaving still at 30° C. After 90 days, it was examined whether the fungi or bacteria were still living or not. As mineral oils, there were used kerosene in Examples 1 and 5, jet fuel in Example 2, gas oil in Examples 4, fuel oil in Examples 6 and 7, and lubricating oil in Example 3. For comparison, a test for examining the growth of fungi or bacteria was conducted by using kerosene, jet fuel, gas oil, fuel oil and lubricating oil including no fungicide. The results of these examples are shown in the following table 2.

These results show that the oil soluble fungicide of this invention is very effective.

Table 2

| Example | Type and concentration of fungicide added to mineral oil | Type of mineral oil used | Sterilizing effect (by cultivation at 30° C. for 90 days) | | | | | | |
|---|---|---|---|---|---|---|---|---|---|
| | | | Cladosporium sp. | Penicillium sp. | Aspergiblus sp. | Fusarium sp. | Paecilomyces sp. | Candida sp. | Pseudomonas sp. |
| | Product of Experiment 1 50 ppm. | kerosene | - No growth of fungi and bacteria was observed - - - - - | | | | | | |
| 2 | Product of Experiment 2 100 ppm. | jet fuel | - Same as above - | | | | | | |
| 3 | Product of Experiment 3 80 ppm. | lubricating oil | - Same as above - | | | | | | |
| 4 | Product of Experiment 4 100 ppm. | Gas oil | - Same as above - | | | | | | |
| 5 | Product of Experiment 5 150 ppm. | kerosene | - Same as above -- | | | | | | |
| 6 | Product of Experiment 6 50 ppm. | fuel oil | - Same as above - | | | | | | |
| 7 | Product of Experiment 7 | fuel oil | - Same as above - | | | | | | |

Table 2-continued

| Example | Type and concentration of fungicide added to mineral oil | Type of mineral oil used | Sterilizing effect (by cultivation at 30° C. for 90 days) | | | | | | |
|---|---|---|---|---|---|---|---|---|---|
| | | | Cladosporium sp. | Penicilliun sp. | Aspergiblus sp. | Fusarium sp. | Paecilomyces sp. | Candida sp. | Pseudomonas sp. |
| | 100 ppm. | | | | | | | | |
| Comparative Example 1 | No fungicide was added | kerosene, jet fuel, gas oil, fuel oil, and lubricating oil. | Large quantity of fungi grew in all boundary surfaces between mineral oils and inorganic culture grounds. | | | | | | |

We claim:

1. An oil soluble fungicide obtained from the process which comprises reacting an aqueous solution of a least one quaternary ammonium salt of the general formula

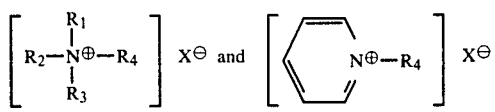

in which $R_1$ of the quaternary cation is a benzyl radical, $R_2$ and $R_3$ of said cation each represent an aliphatic hydrocarbon radical of from 1 to 8 carbon atoms, $R_4$ of said cation is an aliphatic hydrocarbon radical of from 8 to 20 carbon atoms, and the anion $X^-$ is derived from a salt-forming acid, with an alkyl benzene sulfonic acid salt wherein the alkyl moiety contains from 10 to 14 carbon atoms to provide an oil soluble quaternary ammonium sulfonate fungicide.

2. An oil soluble fungicide of claim 1 wherein said fungicide is alkyldimethylbenzylammonium decylbenzene sulfonate in which the alkyl is a mixture of alkyl groups of from 8 to 18 carbon atoms.

3. An oil soluble fungicide of claim 1 wherein said fungicide is alkyldimethylbenzylammonium dodecylbenzene sulfonate in which the alkyl is a mixture of alkyl groups of from 8 to 22 carbon atoms.

4. An oil soluble fungicide of claim 1 wherein said fungicide is the dodecylbenzene sulfonic acid complex of cetyl pyridinium.

5. An oil soluble fungicide of claim 1 wherein said fungicide is alkyldimethylbenzylammonium tetradecylbenzene sulfonate in which the alkyl is a mixture of alkyl groups of from 8 to 18 carbon atoms.

6. An oil soluble fungicide of claim 1 wherein said fungicide is alkyldimethylbenzylammonium tetradecylbenzene sulfonate in which the alkyl is a mixture of alkyl groups of from 8 to 18 carbon atoms.

7. An oil soluble fungicide of claim 1 wherein said fungicide is alkyldimethylbenzylammonium decylbenzene sulfonate in which the alkyl is a mixture of alkyl groups of from 8 to 18 carbon atoms.

8. An oil soluble fungicide of claim 1 wherein the quaternary cation is alkyldimethylbenzylammonium in which the alkyl is a mixture of alkyl groups of from 8 to 18 carbon atoms, and the alkyl moiety of the alkyl benzene sulfonic acid salt is a mixture of alkyl groups of from 10 to 14 carbon atoms.

9. An oil soluble fungicide of claim 1 wherein the quaternary cation is cetyl pyridinium, and the alkyl moiety of the alkyl benzene sulfonic acid salt is a mixture of alkyl groups of from 10 to 14 carbon atoms.

10. An oil containing from about 10 to 10,000 ppm of an oil soluble fungicide prepared by the process of claim 1.

11. The oil of claim 10 wherein said oil is selected from the group consisting of mineral oil, kerosene, jet fuel, gas oil, fuel oil and lubricating oil.

12. The oil of claim 11 wherein the fungicide is alkydimethylbenzylammonium decylbenzene sulfonate in which the alkyl is a mixture of alkyl groups of from 8 to 18 carbon atoms.

13. The oil of claim 11 wherein said fungicide is alkyldimethylbenzylammonium dodecylbenzene sulfonate in which the alkyl is a mixture of alkyl groups of from 8 to 22 carbon atoms.

14. The oil of claim 11 wherein said fungicide is the dodecylbenzene sulfonic acid complex of cetyl pyridinium.

* * * * *